US009050357B2

(12) United States Patent
Yang et al.

(10) Patent No.: US 9,050,357 B2
(45) Date of Patent: Jun. 9, 2015

(54) COMPOSITIONS AND METHODS FOR PRODUCING CONSUMABLES FOR PATIENTS WITH DYSPHAGIA

(75) Inventors: Zhi-Fa Yang, San Diego, CA (US); Todd Talashek, San Diego, CA (US); Wei Li, San Diego, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 946 days.

(21) Appl. No.: 12/719,549

(22) Filed: Mar. 8, 2010

(65) Prior Publication Data
US 2011/0217442 A1 Sep. 8, 2011

(51) Int. Cl.
*A61K 31/723* (2006.01)
*A61K 9/00* (2006.01)
*A61K 47/36* (2006.01)

(52) U.S. Cl.
CPC ............. *A61K 31/723* (2013.01); *A61K 9/0095* (2013.01); *A61K 47/36* (2013.01)

(58) Field of Classification Search
USPC ....................................................... 426/573
See application file for complete search history.

(56) References Cited

U.S. PATENT DOCUMENTS

| | | | |
|---|---|---|---|
| 3,232,929 A | 2/1966 | McNelly et al. | |
| 4,105,461 A | 8/1978 | Racciato | |
| 4,369,125 A | 1/1983 | Kragen et al. | |
| 4,382,966 A | 5/1983 | Mickus et al. | |
| 4,826,700 A | 5/1989 | Bayerlein et al. | |
| 5,250,307 A | 10/1993 | Cummings et al. | |
| 5,550,307 A | 8/1996 | Hope et al. | |
| 5,932,235 A | 8/1999 | Ninomiya et al. | |
| 6,139,895 A | 10/2000 | Zablocki et al. | |
| 6,162,471 A | 12/2000 | Sheldon | |
| 6,277,395 B1 | 8/2001 | Fukui et al. | |
| 6,316,614 B1 | 11/2001 | Doherty et al. | |
| 6,331,540 B1 | 12/2001 | Kabra | |
| 6,436,446 B1 | 8/2002 | Forusz et al. | |
| 6,455,090 B1 | 9/2002 | Uzuhashi et al. | |
| 6,458,395 B1 | 10/2002 | Emoto | |
| 6,586,213 B2 | 7/2003 | Kobzeff et al. | |
| 6,592,863 B2 | 7/2003 | Fuchs et al. | |
| 6,719,967 B1 | 4/2004 | Brown et al. | |
| 6,887,850 B2 | 5/2005 | Fuchs et al. | |
| 2003/0108508 A1 | 6/2003 | Yumioka et al. | |
| 2004/0197456 A1 | 10/2004 | Holahan | |
| 2005/0031685 A1 | 2/2005 | Sen et al. | |
| 2005/0260322 A1* | 11/2005 | Takaichi et al. | 426/573 |
| 2006/0051296 A1 | 3/2006 | Holahan | |
| 2006/0099167 A1 | 5/2006 | Staudigel et al. | |
| 2006/0270650 A1 | 11/2006 | MacNeil et al. | |
| 2007/0087941 A1 | 4/2007 | Cawiezel | |
| 2008/0014307 A1 | 1/2008 | Bailey et al. | |
| 2008/0027024 A1 | 1/2008 | Gahler et al. | |
| 2008/0124439 A1 | 5/2008 | Nuralam | |
| 2008/0139432 A1 | 6/2008 | Peffly et al. | |
| 2008/0248013 A1 | 10/2008 | Ikemoto et al. | |
| 2008/0287300 A1 | 11/2008 | Kopesky | |
| 2009/0041897 A1 | 2/2009 | Gamay | |
| 2009/0074940 A1 | 3/2009 | Sliwinski | |
| 2009/0081351 A1 | 3/2009 | Mellema et al. | |
| 2009/0130213 A1 | 5/2009 | Jain et al. | |
| 2010/0055262 A1 | 3/2010 | Holahan | |
| 2010/0178397 A1 | 7/2010 | Stetzer | |
| 2011/0274629 A1 | 11/2011 | Li et al. | |

FOREIGN PATENT DOCUMENTS

| | | |
|---|---|---|
| EP | 0068706 | 1/1983 |
| EP | 2078460 | 7/2009 |
| JP | 11318356 A | 11/1999 |
| JP | 2002300854 | 10/2002 |
| JP | 2005304378 | 11/2005 |
| JP | 2006197838 A * | 8/2006 |
| JP | 2006006252 | 12/2006 |
| JP | 2008017766 | 1/2008 |
| JP | 2008125435 | 6/2008 |
| JP | 2008154527 | 7/2008 |
| JP | 2008301775 | 12/2008 |
| JP | 2009100667 | 5/2009 |
| WO | 00/61674 | 10/2000 |
| WO | 01/88058 A2 | 11/2001 |
| WO | 2006/054886 | 5/2006 |
| WO | 2008/137181 | 11/2008 |

OTHER PUBLICATIONS

Burdock Group, Reduced Pyruvate Xanthan Gum, Aug. 2006, pp. 1-61 http://www.accessdata.fda.gov/scripts/fcn/gras_notices/615877A.PDF.*

(Continued)

*Primary Examiner* — Kelly Bekker
(74) *Attorney, Agent, or Firm* — Sutherland Asbill & Brennan LLP

(57) ABSTRACT

Compositions are provided that are suitable for safe consumption by a patient with dysphagia. In one embodiment, the compositions include a modified xanthan gum in an amount suitable to provide a viscous, free-flowing solution having gel-like properties. The modified xanthan gum comprises a non-pyruvylated xanthan gum, a reduced-pyruvylated xanthan gum, or a combination thereof. The composition desirably has a viscosity of greater than about 2000 cP and is characterized as having a shape retention of greater than about 50%. Also provided are methods for their preparation and use.

10 Claims, No Drawings

(56) References Cited

OTHER PUBLICATIONS

Karolyn P. Shatwell et al., "Influence of the Acetyl Substituent on the Interaction of Xanthan with Plant Polysaccharides—I. Xanthan—Locust Bean Gum Systems," Carbohydrate Polymers, 1991, pp. 29-51, vol. 14, Elsevier Science Publishers Ltd, England.

I. J. Bradshaw, et al., "Modified Xanthan—Its Preparation and Viscosity," Carbohydrate Polymers, 1983, pp. 23-38, vol. 3, Applied Science Publishers Ltd, England.

Randal A. Hassler et al., "Genetic Engineering of Polysaccharide Structure: Production of Variants of Xanthan Gum in *Xanthomonas campestris*," Biotechnol. Prog. 1990, pp. 182-187, vol. 6, American Chemical Society and American Institute of Chemical Engineers.

Disclosure Under 37 C.F.R. 1.56 dated Aug. 13, 2010, filed for U.S. Appl. No. 12/719,549, pp. 1-12.

PCT International Search Report and Written Opinion for PCT/US2011/027132 mailed Jul. 12, 2011, pp. 1-13.

English translation of the Office Action of Japanese Patent Application No. 2012-557117 dated Aug. 26, 2014, pp. 1-4.

\* cited by examiner

COMPOSITIONS AND METHODS FOR PRODUCING CONSUMABLES FOR PATIENTS WITH DYSPHAGIA

BACKGROUND

Dysphagia is a medical condition that effects millions of people in the United States and internationally. Patients who have dysphagia have difficulty swallowing and may also experience pain while swallowing. In particular, many patients with dysphagia have trouble swallowing liquids, foods, or saliva. Thus, eating and drinking can be a challenge for a patient with dysphagia, making it difficult for the patient to take in enough calories and fluids to nourish the body.

One common method for treating and managing dysphagia is the use of thickening agents (e.g., starch powders, modified starch powders, native xanthan gum, and guar gums) to prepare thickened beverages. Existing thickening agents, however, often have poor dispersibility, are ineffective for thickening many types of solutions at desired use levels, and fail to produce a thickened beverage that has both the required consistency and a desirable mouthfeel and taste.

For example, one frequently used thickening agent is modified corn starch. Modified corn starches, however, produce cloudy beverages and require use at high levels to sufficiently increase the beverage viscosity to the desired levels. When used as these high levels, however, the resulting beverages are pasty and have an undesirable mouthfeel. In addition, the modified corn starches also are typically shear-thickening, making them more difficult for a dysphagia patient to swallow.

Another commonly used thickening agent is native xanthan gums. Xanthan gum is a microbial polysaccharide produced by a pure culture of aerobic submerged fermentation of *Xanthomonas campestris*. Native xanthan gum is comprised of a 1,4 linked D-glucose backbone with trisaccharide side chains on alternating anhydroglucose units. The side chains are comprised of a glucuronic acid residue between two mannose units. Approximately 50% of the terminal mannose molecules carry a pyruvic acid residue. When xanthan gum is hydrated in an aqueous solution at typical gum concentrations (0.1 to 1 wt %) for commercial applications, a viscous but free-flowing solution is obtained. Although the native xanthan gums provide improvements over conventional starch-based thickening agents, there remain other problems with the resulting beverage.

In particular, Applicants have discovered that it is particularly desirable for a thickening agent to be capable of imparting "gel-like" properties to a composition. Gel-like properties are particularly desirable in thickening of drinkable beverages (water, tea, milk, juice, etc.) for dysphagia patients. The "gel-like" properties enable dysphagia patients to safely consume these compositions, allowing for adequate flow in the esophagus while maintaining sufficient cohesiveness that avoids aspiration into the trachea. Prior art thickening agents, however, are ineffective at producing beverages having "gel-like" properties. The use of common gelling agents, such as gellan gum, carrageenan, pectin, gelatin, etc., requires extensive preparation to form gels (e.g., heating and cooling the solutions in the presence of gelling ions). Additionally, gels that are formed using common gelling agents generally are too rigid and do not provide the desired free-flowing solution.

Accordingly, there exists a need for an effective thickening agent capable of imparting both viscous, free-flowing properties and gel-like properties to a composition while also providing a desirable mouthfeel and clarity.

SUMMARY

In one embodiment, a composition suitable for safe consumption by a patient with dysphagia is provided comprising a modified xanthan gum in an amount suitable to provide a viscous, free-flowing solution having gel-like properties, wherein the modified xanthan gum comprises a non-pyruvylated xanthan gum, a reduced-pyruvylated xanthan gum, or a combination thereof, and wherein the composition has a viscosity of greater than about 2000 cP and is characterized as having a shape retention of greater than about 50%.

In another embodiment, a method is provided for preparing a composition for hydrating or providing nutrients or medicaments to a patient with dysphagia comprising adding a modified xanthan gum to an aqueous solution, and mixing the composition, wherein the modified xanthan gum comprises a non-pyruvylated xanthan gum, a reduced-pyruvylated xanthan gum, or a combination thereof, and wherein the composition has a viscosity of greater than about 2000 cP and is characterized as having a shape retention of greater than about 50%.

In still another embodiment, a method is provided for hydrating or providing nutrition or medicament to a patient with dysphagia comprising providing a composition comprising a modified xanthan gum for ingestion by a patient with dysphagia, the composition comprising a modified xanthan gum in an amount suitable to provide a viscous, free-flowing solution having gel-like properties, wherein the modified xanthan gum comprises a non-pyruvylated xanthan gum, a reduced-pyruvylated xanthan gum, or a combination thereof, and wherein the composition has a viscosity of greater than about 2000 cP and is characterized as having a shape retention of greater than about 50%.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Compositions are provided that are suitable for safe consumption by a patient with dysphagia. In particular, compositions are provided comprising a modified xanthan gum in an amount suitable to provide a viscous, free-flowing solution, wherein the modified xanthan gum comprises a non-pyruvylated xanthan gum, a reduced-pyruvylated xanthan gum, or a combination thereof, and wherein the composition is characterized by its gel-like properties.

As used herein, the term "gel-like" refers to a composition having properties between those of a liquid and a gel. A composition having gel-like properties has properties that are characteristic of both a liquid (flow) and a gel (shape retention).

The liquid properties of a composition are characterized by the viscosity of the composition, which may be measured using methods well known to those skilled in the art, which are described in more detail hereinbelow. In an embodiment, a composition is considered to be a viscous, free-flowing solution when it has a viscosity of at least 2000 cP. For example, in one aspect a composition is characterized as being a viscous, free-flowing solution when it has a viscosity of at least 2500 cP, a viscosity of at least 3000 cP, a viscosity of at least 3500 cP, or a viscosity of at least 4000 cP.

The gel-like properties of a composition are characterized by measuring the initial height of the composition using Texture Profile Analysis (TPA), which is described hereinbelow. In an embodiment, a composition is considered to have "gel-like" properties when it retains at least 50% as measured using TPA immediately after having been demolded. For example, in one aspect a composition is characterized as having gel-like properties when it retains at least 60% of its height, at least 70% of its height, at least 80% of its height, at least 90% of its height, or at least 95% of its height.

A. Modified Xanthan Gums

The present description utilizes modified xanthan gums having a lower pyruvate content than that of native xanthan gums, non-limiting examples of which include non-pyruvylated xanthan gums, reduced-pyruvylated xanthan gums, and combinations thereof. Those skilled in the art will appreciate that native xanthan gums generally have a pyruvate content of about 3.0 to about 6.0%. Thus, the modified xanthan gums of the present description may be broadly characterized as having a pyruvate content of less than about 2.0%.

In one embodiment, the modified xanthan gum comprises a non-pyruvylated xanthan gum. A non-pyruvylated xanthan gum (NPX), as used herein, comprises a modified xanthan gum having substantially no pyruvate. Substantially no pyruvate, as used herein, means a pyruvate content of up to about 0.5%.

In one embodiment, the modified xanthan gum comprises a reduced-pyruvylated xanthan gum. A reduced-pyruvylated xanthan gum (RPX), as used herein, comprises a modified xanthan gum having a pyruvate content up to about 2.0%. That is, a reduced-pyruvylated xanthan gum generally comprises a modified xanthan gum having a pyruvate content greater than the non-pyruvylated xanthan gum (up to about 0.5%) and less than the pyruvate content of native xanthan gums (greater than about 2.0%). For example, a reduced-pyruvylated xanthan gum according to embodiments provided herein comprises a pyruvate content of about 0.5% to about 2.0%, a pyruvate content of about 0.5% to about 1.5%, or a pyruvate content of about 0.5% to about 1.0%.

Applicants surprisingly have discovered that the modified xanthan gums having lower levels of pyruvate than native xanthan gums behave differently than the native xanthan gums in a manner that was not appreciated in the prior art and that would not have been expected based on the teachings of the prior art. In particular, the modified xanthan gums provided in the present description are capable of imparting gel-like properties to compositions. For example, a composition having 1% NPX (w/w) provided a composition having a much higher viscosity and gel-like characteristics when compared to a composition having 1% native xanthan gum (w/w).

Although the modified xanthan gums of the present description are known for use in unrelated applications, it was not known or predicted that use of the modified xanthan gums would impart gel-like properties to compositions and therefore would be particularly suitable for use in dysphagia applications. As illustrated in the examples herein below, the modified xanthan gums of the present description provide surprisingly improved gel-like properties as compared to the native xanthan gums of the prior art.

B. Measurement of Liquid Properties

As noted above, the liquid properties of a composition are evaluated by measuring the viscosity of the composition using methods well known to those skilled in the art. In an embodiment, the viscosity can be measured using a Brookfield LV-type viscometer at 30 rpm using a disk-shaped spindle #63. The relative viscosity can then be evaluated by calculating the ratio of the viscosity of a modified xanthan gum composition to the viscosity of a native xanthan gum composition at the same concentration. For example, if a modified xanthan gum composition (1% by weight) has a viscosity of 3000 cP and a native xanthan gum composition (1% by weight) has a viscosity of 1500 cP, the modified xanthan gum composition has a relative viscosity of 2.0.

In one aspect a modified xanthan gum composition provided herein has a relative viscosity of greater than about 1.0. In another aspect, a modified xanthan gum composition has a relative viscosity of greater than about 1.25, greater than about 1.5, greater than about 1.75, greater than about 2.0, greater than about 2.5, greater than about 3.0, greater than about 3.5, greater than about 4.0, or greater than about 5.0. In another aspect, a modified xanthan gum composition has a relative viscosity in the range of about 1.0 to about 10.0, in the range of about 2.0 to about 9.0, in the range of about 3.0 to about 8.0, in the range of about 3.0 to about 7.0, or in the range of about 3.0 to about 6.0.

C. Measurement of Gel-Like Properties

Whether a composition has gel-like properties is evaluated using Texture Profile Analysis (TPA), which is conventionally used for characterizing gels (see http://www.texturetechnologies.com/texture_profile_analysis.html for references using TPA). A key parameter for assessing "gel-like" properties is the height of the composition after de-molding, which indicates the composition's ability to retain its initial shape.

A composition is prepared and poured into the acrylic ring molds (internal diameter: 29 mm; height: 12 mm). The composition is subsequently de-molded from the acrylic ring mold and the height of the composition is immediately measured. (See Examples below). The greater the height (relative to the height of the acrylic ring mold), the more "gel-like" the composition.

D. Preparation of Modified Xanthan Gums

The modified xanthan gums of the present description can be prepared by fermentation of any strain capable of producing a modified xanthan gum having a lower pyruvate content than that of native xanthan gums. For example, a suitable modified xanthan gum can be produced using the non-pyruvate *Xanthomonas campestris* (See U.S. Pat. No. 6,316,614 and *Biotechnol. Prog.* 1990, 6, 182-187 for descriptions on a similar strain) or the low (reduced) pyruvate *Xanthomonas campestris* (See *Carbohydrate Polymers* 1991, 14, 29-51 for a similar type of naturally-occurring mutant). Additionally, pyruvate substituents can be removed from native xanthan gums by chemical treatment. (See *Carbohydrate Polymers*, 1983, 3, 23-38).

Non-limiting examples of strains capable of producing non-pyruvylated xanthan gum include ATCC deposits 53472 and 67344. (See U.S. Pat. No. 6,316,614).

Non-limiting examples of strains capable of producing reduced-pyruvyated xanthan gum include ATCC deposits 53474. (See Id.).

The modified xanthan gum can then be recovered from the fermentation broth and treated using methods known to those skilled in the art (e.g., clarification, pasteurization, precipitation, drying, milling).

E. Compositions for Use of Modified Xanthan Gums

The modified xanthan gums provided herein can be used in any composition in which it is desired to provide a viscous, free-flowing solution having gel-like properties. Those skilled in the art should appreciate that the amount of the modified xanthan gum used in the composition can be modified depending upon the desired properties of the resulting composition. In embodiments, the modified xanthan gum is added to the composition in an amount from about 0.5% to about 2.0% (w/w) of the final composition.

The modified xanthan gums provided herein also can be combined with other ingredients before being added to compositions for consumption by a patient with dysphagia, non-limiting examples of which include dispersants and other thickeners (e.g., guar), salts, etc.

In one embodiment, the modified xanthan gum is combined with a dispersing agent prior to addition of the modified xanthan gum to a composition for consumption by a patient with dysphagia. Any dispersing agent, which functions to aid in the dispersion of the modified xanthan gum in the composition for consumption by a patient with dysphagia, which does not interfere with the functional properties of the modified xanthan gum, and which is approved for human consumption, can be used. Non-limiting examples of suitable dispersing agents include dextrin or maltodextrin; low molecular weight sugars such as dextrose, sucrose, and maltose; sugar alcohols such as sorbitol and mannitol; silicon dioxide; and tricalcium phosphate.

Not wishing to be bound by any theory, it also is believed that the modified xanthan gums provided herein are suitable for use as thickening agents in other compositions in which it is desirable to impart gel-like properties. For example, the modified xanthan gum also may be useful in foodstuffs such as low fat mayonnaise, spoonable dressings, sauces, yogurt, cream cheese, low fat spreads, and beverages.

F. Methods of Use of Modified Xanthan Gums

The modified xanthan gums provided herein may be added to compositions in an appropriate amount and using any suitable method capable of providing a composition having the desired "gel-like" properties.

In one embodiment, the modified xanthan gums may be added to an aqueous composition and dispersed within the aqueous composition using any suitable method of mixing. For example, in an embodiment the method of mixing may comprise approximately 30 seconds of low shear hand mixing at ambient temperature to provide for the rapid hydration of the modified xanthan gums in the aqueous composition. Those skilled in the art will appreciate that many of the currently available thickening agents for dysphagic patients require significantly more complex methods of preparation. Thus, the modified xanthan gums provided herein enable for the simple and effective preparation of aqueous compositions having gel-like properties that are suitable for consumption by a patient with dysphagia.

In one embodiment, the modified xanthan gums may be provided in the form of a product that may be provided for dysphagia patients to utilize at home or in an inpatient setting. For example, the modified xanthan gums may be provided in a packet containing a pre-measured amount of the modified xanthan gums and a dispersion agent. This packet may, for example, be opened, added to a desired beverage, foodstuff or medicament, and then briefly hand mixed into the foodstuff or medicament to provide a composition having a desired viscosity and gel-like properties for the dysphagia patient to safely ingest.

The present disclosure is further illustrated by the following examples, which are not to be construed in any way as imposing limitations upon the scope thereof. On the contrary, it is to be clearly understood that resort may be had to various other embodiments, modifications and equivalents thereof which, after reading the description therein, may suggestion themselves to those skilled in the art without departing from the spirit of the present invention and/or the scope of the appended claims.

Examples

Native Xanthan Gum (NXG) Preparation

Native xanthan gum was prepared from a standard xanthan fermentation broth (e.g., U.S. Pat. No. 3,232,929) produced in a 30,000 gallon fermentor, treated with a standard enzyme clarification process (e.g., U.S. Pat. No. 6,586,213), and recovered by conventional pasteurization, precipitation, drying and milling. The native xanthan gums 1 and 2 had a pyruvate content of between about 4 and about 5%.

Non-Pyruvylated Xanthan Gum (NPX) Preparation

Non-pyruvylated xanthan gum was prepared from a non-pyruvate strain (e.g., U.S. Pat. No. 6,316,614 for a similar type strain) produced in a 1200 gallon fermentor, treated with a standard enzyme clarification process, and recovered by conventional pasteurization, precipitation, drying and milling. Replicates NPX 1, NPX 2, NPX 3, and NPX 4 each had a pyruvate content of less than 0.5% by weight.

Reduced-Pyruvylated Xanthan Gum (RPX) Preparation

Reduced-pyruvylated xanthan gum was prepared from a low pyruvate strain (a spontaneous mutant strain isolated from a standard xanthan strain) produced in a 1200 gallon fermentor, treated with a standard enzyme clarification process, and recovered by conventional pasteurization, precipitation, drying and milling. RPX 1 had a pyruvate content of approximately 2% by weight.

Native and Modified Xanthan Gum Compositions

Homogeneous dry powders were prepared of a native xanthan gum, non-pyruvylated xanthan gum (NPX) or reduced-pyruvylated xanthan gum (RPX) (1.0, 2.0, 2.4, 3.0 or 4.0 g) and dextrin (10.0 g). The dry powder blend was added into 200.0 g of synthetic tap water, (prepared by adding sodium, Na: 1.9 mg/100 ml, and calcium, Ca: 1.6 mg/100 ml, as chloride salts to deionized water) by mixing with a 4-prong propeller mixer at 500 rpm. The dry blend was continuously added to the synthetic tap water over a period of 10 seconds and allowed to mix for a total of 30 seconds. The solution was immediately removed from the mixer and poured into a 180 ml tall form beaker. The hydrated sample was held at room temperature for 1.5 minutes, and the viscosity and shape retention of the solution were immediately evaluated and are summarized below.

The viscosity of the solution was measured with a Brookfield LV-type viscometer at 30 rpm using a disk-shaped spindle #63. The viscosity was recorded after one minute of rotation at ambient temperature.

The shape retention of the solution was measured by TPA. Immediately after measuring the viscosity, the solution was poured into 3 acrylic ring molds (diameter: 29 mm; height: 12 mm). Each molded solution was then de-molded onto a measuring plate and the height of the molded sample was immediately measured using a TA-X2.Ti texture analyzer (Texture Technologies, Scarsdale, N.Y.). The height of the demolded solution on the plate represented the ability of the sample to retain its shape.

| Thickening Agent | Amount (% by weight) | Viscosity (cP) | Relative Viscosity^ | Height (mm) | Shape Retention (% Height) |
|---|---|---|---|---|---|
| Native xanthan 1 | 0.5% | 746 ± 8 | — | 3.37 ± 0.01 | 28.1% |
| Native xanthan 1 | 1.0% | 1547 ± 24 | — | 4.74 ± 0.21 | 39.5% |
| Native xanthan 1 | 1.2% | 1794 ± 3 | — | 5.03 ± 0.12 | 41.9% |
| Native xanthan 1 | 1.5% | 2044 ± 51 | — | 5.16 ± 0.21 | 43.0% |
| Native xanthan 1 | 2.0% | 2766 ± 42 | — | 6.03 ± 0.19 | 50.2% |
| Native xanthan 2 | 1.0% | 1586 ± 14 | — | 4.63 ± 0.20 | 38.6% |
| Native xanthan 2 | 1.2% | 1846 ± 20 | — | 4.76 ± 0.09 | 39.7% |
| Native xanthan 2 | 1.5% | 2284 ± 23 | — | 5.35 ± 0.02 | 44.6% |
| NPX 1 | 0.5% | 2124 ± 34 | 2.8 | 4.63 ± 0.15 | 38.6% |
| NPX 1 | 1.0% | 6050 | 3.9 | 7.85 ± 0.21 | 65.4% |
| NPX 1 | 1.5% | 9850 | 4.82 | 10.14 ± 0.44 | 84.5% |
| NPX 1 | 2.0% | >10000* | >3.62 | 11.21 ± 0.13 | 93.4% |
| NPX 2 | 1.0% | 4940 | 3.2 | 6.88 ± 0.01 | 57.3% |
| NPX 3 | 1.0% | 4810 | 3.1 | 7.31 ± 0.06 | 60.9% |
| NPX 4 | 1.0% | 3671 ± 58 | 2.4 | 6.96 ± 0.04 | 58.0% |
| RPX 1 | 1.0% | 2320 | 1.5 | 5.48 | 45.7% |

*The maximum viscosity that can be measured with the Brookfield LV-type viscometer using spindle #63 at 30 rpm is 10,000 cP.
^ Relative Viscosity to Native xanthan 1 at same concentration As the foregoing illustrates, the modified xanthan gums provided significant improvements to both the viscosity and gel-like properties of the compositions when compared to compositions having comparable amounts of native xanthan gums. For example, compositions prepared using both native xanthan gums (1.0% by weight) had viscosities of less than 1600 cP and shape retention of less than 40% as compared to the compositions prepared using non-pyruvylated xanthan gums (1.0% by weight) which had viscosities of greater than 3600 cP and shape retention of greater than 58%.

It should be apparent that the foregoing relates only to the preferred embodiments of the present invention and that numerous changes and modifications may be made herein without departing from the spirit and the scope of the invention as defined by the following claims and equivalents thereof.

What is claimed is:

1. A composition suitable for safe consumption by a patient with dysphagia comprising a modified xanthan gum that is present in the composition in an amount from about 0.5% to about 2.0% (w/w) of the composition, wherein the modified xanthan gum comprises a non-pyruvylated xanthan gum, a reduced-pyruvylated xanthan gum, or a combination thereof, and wherein the composition has a viscosity of greater than about 2000 cP at ambient temperature and is characterized as having a shape retention of greater than about 50%.

2. The composition of claim 1, wherein the modified xanthan gum is present in the composition in an amount from about 0.5% to about 1.0% (w/w) of the composition.

3. The composition of claim 1, wherein the composition has a viscosity of greater than about 2500 cP at ambient temperature.

4. The composition of claim 1, wherein the composition has a viscosity of greater than about 4000 cP at ambient temperature.

5. The composition of claim 1, wherein the composition is characterized as having a shape retention of greater than 60%.

6. The composition of claim 1, wherein the composition is characterized as having a shape retention of greater 70%.

7. The composition of claim 1, wherein the modified xanthan gum has a pyruvate content of less than about 2.0% by weight.

8. The composition of claim 1, wherein the modified xanthan gum has a pyruvate content of less than about 1.5% by weight.

9. The composition of claim 1, wherein the modified xanthan gum has a pyruvate content of less than about 1.0% by weight.

10. The composition of claim 1, wherein the modified xanthan gum has a pyruvate content of less than about 0.5% by weight.

* * * * *